US007056883B2

(12) United States Patent
Ito et al.

(10) Patent No.: US 7,056,883 B2
(45) Date of Patent: Jun. 6, 2006

(54) THERAPEUTIC AGENT FOR SOFT TISSUE SARCOMA

(75) Inventors: Tatsuo Ito, Okayama (JP); Toshifumi Ozaki, Okayama (JP); Mamoru Ouchida, Okayama (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/875,382

(22) Filed: Jun. 25, 2004

(65) Prior Publication Data

US 2005/0107290 A1    May 19, 2005

(30) Foreign Application Priority Data

Jun. 27, 2003   (JP)   ............................. 2003-183643

(51) Int. Cl.
*A61K 38/12* (2006.01)
*A61K 38/00* (2006.01)
*C07K 2/00* (2006.01)
*C07K 7/64* (2006.01)

(52) U.S. Cl. .............................. 514/9; 514/2; 530/300; 530/317

(58) Field of Classification Search .................... 514/9; 530/317

See application file for complete search history.

(56) References Cited

U.S. PATENT DOCUMENTS

| 4,977,138 | A | 12/1990 | Okuhara et al. |
| 6,403,555 | B1 | 6/2002 | Skov |
| 6,905,669 | B1 | 6/2005 | DiMartino |
| 2002/0192727 | A1 | 12/2002 | Setaluri et al. |
| 2004/0053820 | A1* | 3/2004 | Nakajima et al. ............... 514/9 |

FOREIGN PATENT DOCUMENTS

| EP | 0 196 415 A2 | 10/1986 |
| EP | 0 352 646 A2 | 1/1990 |
| EP | 1 302 476 A1 | 4/2003 |
| EP | 1426054 A1 * | 6/2004 |
| JP | 60149520 A * | 8/1985 |
| WO | WO 95/31977 | 11/1995 |
| WO | WO 98/39965 | 9/1998 |
| WO | WO 02/06307 | 1/2002 |
| WO | WO 02/085400 A1 | 10/2002 |
| WO | WO 02/085883 A1 | 10/2002 |
| WO | WO 03/015810 A1 | 2/2003 |
| WO | WO 2003015810 A1 * | 2/2003 |
| WO | WO 03/088954 A1 | 10/2003 |
| WO | WO 2004/075859 A2 | 9/2004 |

OTHER PUBLICATIONS

C Gorman, et al. The Hype and the Hope. Time (1998) 151(19). pp. 40-44. Included HTML copy referenced pp. 1-9.*
T Gura. Systems for Identifying New Drugs are Often Faulty. Science (1997) 278 (Nov. 7), pp. 1041-1042.*
GB Dermer. Another Anniversary for the War on Cancer. Bio/Technology (Mar. 12, 1994). p. 320.*
R McKie. Cancer Research Set Back a Decade. The Observer Jun. 10, 2001. pp. 1-4 (HTML text).*
J.M. Holand and E.Frei. Cancer Medicine, 5th Edition, Bast, et al. Ed. B.C. Decker Inc. Ontario. (2000). 24 pages.*
K. Kusuzaki, et al. Photochem. Photobiol. (2005) preprint published Feb. 1, 2005. 16 pages.*
R.R. Frey, et al. Bioorg. Med. Chem. Letters (2002), pp. 3443-3447.*
A. Kawai, et al. Cancer Letters (2004), pp. 105-113.*
M. Jung. Curr. Med. Chem. (2001), pp. 1505-1511.*
G. Ranjgolikar, et al. Breast Cancer Res. Treat. (1998), pp. 29-38.*
Y. Sasakawa, et al. Biochem. Pharm. (2003), pp. 897-906.*
Y. Sasakawa, et al. Cancer Letters. (2003), pp. 161-168.*
R. Furumai, et al. Cancer Res. (2002), pp. 4916-4921.*
H.J. Kwon, et al. Int. J. Cancer (2002), pp. 290-296.*
W.-G. Zhu and G.A. Otterson. Curr. Med. Chem. (2003), pp. 187-199.*
M. Murata, et al. Jpn. J. Cancer. Res. (2000), pp. 1154-1160.*
M.E. Goldsmith, et al. Clin. Cancer Res. (2003), pp. 5394-5401.*
P.A. Voute, et al. Ann. Oncol. (1999), pp. 1211-1218.*
M.H.M. Schwarzbach, et al. Int. J. Oncol. (2002), pp. 1211-1218.*
W.K. Kelly, et al. "Histone deacetylase inhibitors: from target to clinical trials" Expert Opinion on Investigational Drugs.(2002) vol. 11, No. 12, pp. 1695-1713.*

(Continued)

*Primary Examiner*—Bruce R. Campell
*Assistant Examiner*—Andrew D. Kosar
(74) *Attorney, Agent, or Firm*—Oblon, Spivak, McClelland, Maier & Neustadt, P.C.

(57) ABSTRACT

A therapeutic agent for soft tissue sarcoma (particularly synovial sarcoma), contains a histone deacetylase inhibitor (particularly a compound of formula I) as an active ingredient

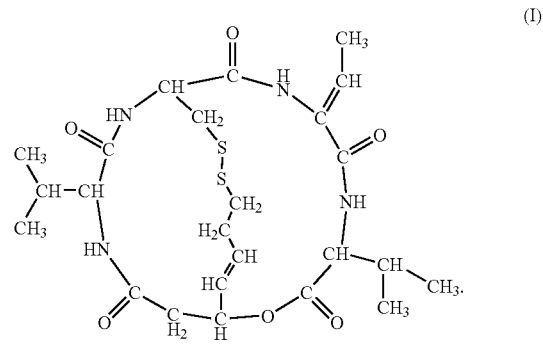

(I)

6 Claims, 5 Drawing Sheets

OTHER PUBLICATIONS

H. Nakajima, et al., Experimental Cell Research, vol. 241, pp. 126-133, "FR901228, A Potent Antitumor Antibiotic, is a Novel Histone Deacetylase Inhibitor", 1998.

K. W. Li, et al., J. Am. Chem. Soc., vol. 118, No. 30, pp. 7237-7238, "Total Synthesis of the Antitumor Depsipeptide FR-901,228", 1996.

H. Ueda, et al., The Journal of Antibiotics, vol. 47, No. 3, pp. 315-323, "FR901228, A Novel Antitumor Bicyclic Depsipeptide Produced by Chromobacterium Violaceum No. 968. III. Antitumor Activities on Experimental Tumors in Mice", Mar. 1994.

H. Kosugi, et al., Jpn. J. Cancer. Res., vol. 92, pp. 529-536, "In Vivo Effects of a Histone Deacetylase Inhibitor, FK228, on Human Acute Promyelocytic Leukemia in NOD/SHI-SCID/SCID Mice", May 2001.

R. L. Piekarz, et al., Blood, vol. 98, No. 9, pp. 2865-2868, "Inhibitor of Histone Deacetylation, Depsipeptide (FR901228), in the Treatment of Peripheral and Cutaneous T-Cell Lymphoma: A Case Report", Nov. 2001.

Y. Sasakawa, et al., Biochemical Pharmacology, vol. 64, pp. 1079-1090, "Effects of FK228, A Novel Histone Deacetylase Inhibitor, on Human Lymphoma U-937 Cells In Vitro and In Vivo", 2002.

M. S. Finnin, et al., NATURE, vol. 401, pp. 188-193, "Structures of a Histone Deacetylase Homologue Bound to the TSA and SAHA Inhibitors", Sep. 9, 1999.

J. E. Eid, et al., Cell, vol. 102, pp. 839-848, "P300 Interacts with the Nuclear Proto-Oncoprotein SYT as Part of the Active Control of Cell Adhesion", Sep. 15, 2000.

H. Kato, et al., The Journal of Biological Chemistry, vol. 277, No. 7, pp. 5498-5505. "SYT Associates with Human SNF/SWI Complexes and the C-Terminal Region of its Fusion Partner SSX1 Targets Histones", Feb. 15, 2002.

C. Thaete, et al., Human Molecular Genetics, vol. 8, No. 4, pp. 585-591, "Functional Domains of the SYT and SYT-SSX Synovial Sarcoma Translocation Proteins and Co-Localization with the SNF Protein BRM in the Nucleus", 1999.

Zhu, Wei-Guo and Otterson, Gregory A., "The Interaction of Histone Deacetylase Inhibitors and DNA Methyltransferase Inhibitors in the Treatment of Human Cancer Cells," Curr. Med. Chem.—Anti-Cancer Agenst, 2003, 3, pp. 187-199.

Michael Curtin, et al., "Histone Deacelytase Inhibitors: The Abbott Experience", Current Medicinal Chemistry, vol. 10, No. 22, XP-008039441, 2003, pp. 2373-2392.

Martha C. Kutko, et al., Histone Deacetylase Inhibitors Induce Growth Suppression and Cell Death in Human Rhabdomyosarcoma in Vitro, Clinical Cancer Research, vol. 9, No. 15, XP-008039438, Nov. 15, 2003, pp. 5749-5755.

Jerry Jaboin, et al., "MS-27-275, an Inhibitor of Histone Deacetylase, Has Marked in Vitro and in Vivo Antitumor Activity Against Pediatric Solid Tumors", Cancer Research, vol. 62, No. 21, XP-001202151, Nov. 1, 2002, pp. 6108-6115.

You Mie Lee, et al., "Inhibition of hypoxia-induced angiogenesis by FK228, a specific histone deacetylase inhibitor, via suppression of HIF-1α activity", Biochemical and Biophysical Research Communications, vol. 300, No. 1, XP-001202149, 2003, pp. 241-246.

Menachem Ailenberg, et al., "Differential effects of trichostatin A on gelatinase A expression in 3T3 fibroblasts and HT-1080 fibrosarcoma cells: Implications for use of TSA in Cancer therapy", Biochemical and Biophysical Research Communications, vol 302, No. 2, XP-008039399, 2003, pp. 181-185.

Hirotsugu Ueda, et al., "FR901228, A Novel Antihumor Bicyclic Depsipeptide Produced by Chromabacterium violaceum No. 968", The Journal of Antibiotics, vol. 47, No. 3, XP-002960289, Mar. 1994, pp. 315-323.

* cited by examiner

… … …

THERAPEUTIC AGENT FOR SOFT TISSUE SARCOMA

TECHNICAL FIELD

The present invention relates to a therapeutic agent for soft tissue sarcoma, which contains a histone deacetylase inhibitor as an active ingredient.

BACKGROUND ART

In general, when there is a report on a substance or a compound having an antitumor activity and the report is based solely on in vitro results, it has been pointed out that such reported results do not directly suggest in vivo results. In other words, a substance showing an antitumor activity in vitro does not necessarily show an antitumor activity in vivo, and application of a substance showing an antitumor activity in vitro directly as an antitumor agent is difficult.

For example, it has been reported that a compound represented by the formula (I)

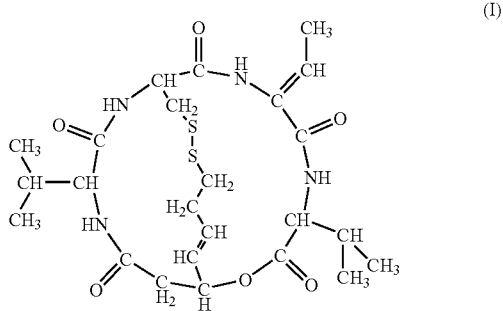

(I)

(hereinafter to be also referred to as compound A; SEQ ID NO: 1), particularly a stereoisomer of the formula (II)

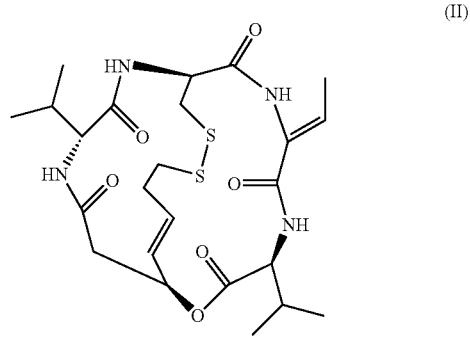

(II)

(hereinafter to be also referred to as compound B or FK228), selectively inhibits histone deacetylase to derive a potent antitumor activity, and that this substance causes high acetylation of histone in the treated cells, thereby inducing transcription-regulatory activity of various genes, cell cycle inhibitory activity and apoptosis (e.g., JP-B-7-64872 (corresponding to U.S. Pat. No. 4,977,138), "Experimental Cell Research", US (1998), vol. 241, pp. 126–133). As the situation now stands, however, there are many problems yet to be solved, such as whether or not in vitro results are directly applicable in vivo, whether or not a useful in vivo effect can be afforded in any tumor, and the like. No report has ever verified in vitro and in vivo antitumor activities against soft tissue sarcoma (particularly synovial sarcoma) of the present invention.

Histone deacetylase is a metallo-deacetylating enzyme coordinating Zn at an active center (M. S. Finnin et al., Nature, 401, 188–193 (1999)). This enzyme is considered to change affinity of various acetylated histones for DNA. The direct biological phenomenon brought thereby is a change in the chromatin structure. The minimum unit of the chromatin structure is a nucleosome wherein 146 bp DNA is wound 1.8 times anticlockwise around a histone octamer (H2A, H2B, H3 and H4, each 2 molecules, core histone). The core histone stabilizes the nucleosome structure by interaction of the positive charge of the N-terminus of each histone protein with DNA. Acetylation of histone is controlled by the equilibrium between an acetylation reaction involving histone acetyltransferase and a deacetylation reaction involving histone deacetylase. It is considered that the histone acetylation occurs at a lysin residue where the histone protein N-terminus is evolutionally preserved well, due to which a core histone protein loses charges at the N-terminus, interaction with DNA is attenuated, and the structure of nucleosome becomes unstable. Accordingly, the histone deacetylation is considered to be the reverse thereof, namely, a shift toward stabilization of the nucleosome structure. However, to what degree the acetylation changes the chromatin structure and how it relates to the transcriptional regulation etc. secondarily induced thereby are unclear in many aspects.

As genetic characteristics of synovial sarcoma, it has been reported that, in about 97% of the entire synovial sarcomas, SYT gene present in the 18th chromosome and SSX gene present on the X chromosome are fused due to chromosomal translocation t (18,X) to express a chimera protein called SYT-SSX, and SYT protein constituting the N-terminal region of this protein is bound with a chromatin remodeling-associated protein such as p300 and BRM to form a complex (Josiane E. Eid et al., Cell, 102, 839–848 (2000)). Synovial sarcoma is one kind of soft tissue sarcoma developed in the four limbs and trunk of the body of males and females, and its primary therapy includes removal of tumor by operation and chemotherapy before and after the operation. However, chemotherapy is associated with poor prognosis and a five-year survival rate is about 60–70%. Thus, an effective cure has not been established as yet.

DISCLOSURE OF THE INVENTION

An object of the present invention is to provide a therapeutic agent for soft tissue sarcoma (particularly synovial sarcoma), which contains a histone deacetylase inhibitor, particularly compound A, compound B, its reduction products, metabolites, derivatives, prodrugs, and other analogs known to have a strong histone deacetylase inhibitory activity, or a pharmaceutically acceptable salt thereof, as an active ingredient.

In an attempt to solve the above-mentioned problems, the present inventors have considered that, in synovial sarcoma, formation of the aforementioned complex of SYT-SSX protein, a chromatin remodeling-associated protein and histone deacetylase (HDAC)-associated protein enhances histone deacetylase activity, which in turn has an effect on the canceration, development and/or proliferation, of synovial sarcoma, and have conducted intensive studies of the effect of histone deacetylase inhibition on various synovial sarcoma cell strains (HS-SY-2, YaFuSS, SYO-1) that express SYT-SSX protein. As a result, they have found that compound B and tricostatin A, which are histone deacetylase inhibitors, exhibit a potent antitumor activity in vitro and in vivo against SYT-SSX protein expressing cells. Furthermore, they have found that they also exhibit a potent antitumor activity against a synovial sarcoma cell strain (HTB93: which is the ATCC identification number of cell line SW982) not expressing SYT-SSX protein. Accordingly, the present invention provides the following.

(1) A therapeutic agent for soft tissue sarcoma, which comprises a histone deacetylase inhibitor as an active ingredient.
(2) The therapeutic agent of the above-mentioned (1), wherein the soft tissue sarcoma is synovial sarcoma.
(3) The therapeutic agent of the above-mentioned (1) or (2), wherein the soft tissue sarcoma or synovial sarcoma is an SYT-SSX protein expressing sarcoma.
(4) The therapeutic agent of the above-mentioned (1), wherein the histone deacetylase inhibitor is compound A or compound B, or a reduced form thereof, an analog thereof, a prodrug thereof or a pharmaceutically acceptable salt thereof.
(5) The therapeutic agent of the above-mentioned (4), wherein the soft tissue sarcoma is synovial sarcoma.
(6) The therapeutic agent of the above-mentioned (5), wherein the synovial sarcoma is SYT-SSX protein expressing sarcoma.
(7) A pharmaceutical composition for the treatment of soft tissue sarcoma, which comprises a histone deacetylase inhibitor and a pharmaceutically acceptable carrier.
(8) The pharmaceutical composition of the above-mentioned (7), wherein the histone deacetylase inhibitor is compound A or compound B, or a reduced form thereof, an analog thereof, a prodrug thereof or a pharmaceutically acceptable salt thereof.
(9) A method for treating soft tissue sarcoma, synovial sarcoma, or an SYT-SSX protein expressing sarcoma, which comprises administering an effective amount of a histone deacetylase inhibitor.
(10) The method of the above-mentioned (9), wherein the histone deacetylase inhibitor is compound A or compound B, or a reduced form thereof, an analog thereof, a prodrug thereof or a pharmaceutically acceptable salt thereof.
(11) Use of a histone deacetylase inhibitor for the production of a therapeutic agent for soft tissue sarcoma.
(12) The use of the above-mentioned (11), wherein the histone deacetylase inhibitor is compound A or compound B, or a reduced form thereof, an analog thereof, a prodrug thereof or a pharmaceutically acceptable salt thereof.
(13) A commercial package comprising the pharmaceutical composition of the above-mentioned (7) and a written matter associated therewith, the written matter stating that said pharmaceutical composition can or should be used for the treatment of soft tissue sarcoma.

DETAILED DESCRIPTION OF THE INVENTION

Figure 1:
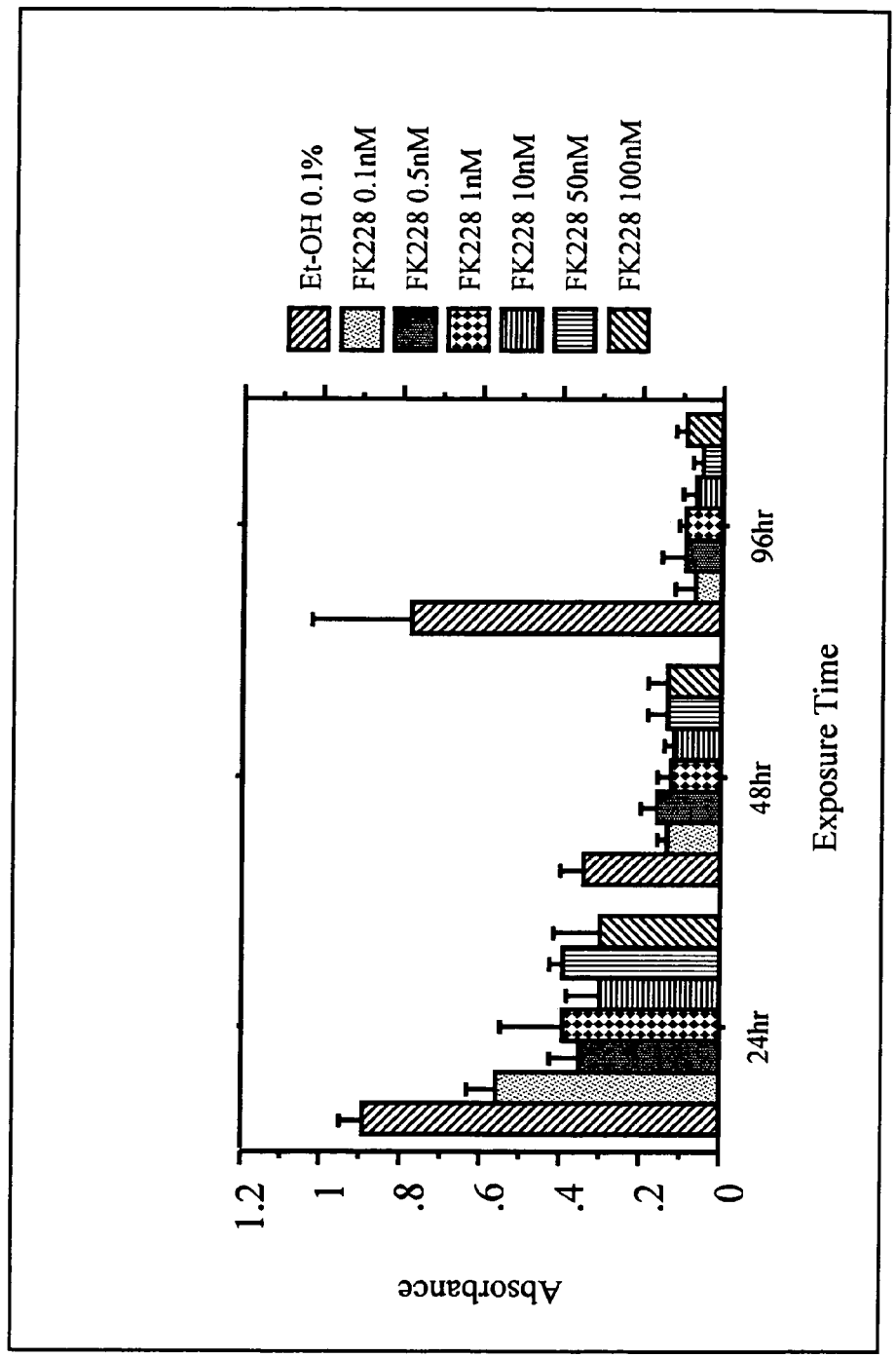
FIG. 1 is a graph showing an in vitro antitumor action of FK228 against HS-SY-2 synovial sarcoma cell strain, which is one of the SYT-SSX protein expressing synovial sarcoma cell strains.

The "histone deacetylase inhibitor", also referred to as "HDAC inhibitor" or "HDACi", in the present invention is a compound that binds to an active site of histone deacetylase competitively with substrates, and/or a compound that reduces or inhibits the enzyme activity of histone deacetylase, and includes any compound (whether synthetic or natural) reported or will be reported in the future to have a histone deacetylase inhibitory activity. To be specific, the aforementioned compound A, a salt thereof and a derivative thereof (e.g., acetylated compound A, thiol form (reduced form) with reduced S—S bond as described in WO02/06307, analogs thereof (e.g., compounds described in U.S. Pat. No. 6,403,555 etc.), prodrugs thereof, etc.) can be mentioned. In addition, Trichostatin A, sodium butyrate, suberoylanilide hydroxamic acid (SAHA), MS-275, cyclic hydroxamic-acid-containing peptide, Apicidin, Trapoxin and the like are the compounds reported to have a histone deacetylase inhibitory activity.

While compound A (and other HDACi's) may have a stereoisomer (e.g., compound B) based on an asymmetric carbon atom or a double bond, such as an optically active form, a geometric isomer and the like, all these isomers and mixtures thereof are also encompassed in the scope of the histone deacetylase inhibitor to be used in the present invention.

In the present specification, unless particularly specified, a simple reference to compound A means a group of compounds regardless of stereoisomerism, which include a compound B represented by the formula (II).

Moreover, solvate compounds (e.g., inclusion compounds (e.g., hydrate etc.)), anhydrous forms, other crystal polymorphs and pharmaceutically acceptable salts thereof of HDACi's, such as compound A, compound B and salts thereof, are also encompassed in the scope of the present invention.

The compound A or a salt thereof are known and available substances. For example, compound B, which is one of the stereoisomers of compound A, can be obtained by culturing a strain belonging to the genus *Chromobacterium*, which is capable of producing compound B, under aerobic conditions, and harvesting the substance from its culture broth. As the strain belonging to the genus *Chromobacterium*, which is capable of producing compound B, for example, *Chromobacterium violaceum* WB968 (FERM BP-1968) can be mentioned. More specifically, compound B can be obtained from a compound B producing strain as described in JP-B-7-64872 (corresponding to U.S. Pat. No. 4,977,138). The compound B is preferably harvested from a strain belonging to the genus *Chromobacterium*, which is capable of producing compound B, because it can be obtained more easily. Synthetic or semi-synthetic compound B is also advantageous in that further purification step is not necessary or the number of steps can be reduced. Similarly, compounds A other than compound B can be also obtained by semi-synthesis or total synthesis by conventionally known methods. To be more specific, it can be produced according to the method reported by Khan W. Li, et al. (J. Am. Chem. Soc., Vol. 118, 7237–7238(1996)).

A pharmaceutically acceptable salt of HDACi's, such as the salt of compound A or compound B, includes salts with a base or an acid addition salt such as salts with inorganic base (e.g., alkali metal salts such as sodium salt, potassium salt etc., alkaline earth metal salts such as calcium salt, magnesium salt etc., ammonium salt), salts with an organic base (e.g., organic amine salts such as triethylamine salt, diisopropylethylamine salt, pyridine salt, picoline salt, ethanolamine salt, triethanolamine salt, dicyclohexylamine salt, N,N'-dibenzylethylenediamine salt etc.), inorganic acid addition salts (e.g., hydrochloride, hydrobromide, sulfate, phosphate etc.), organic carboxylic acid or sulfonic acid addition salts (e.g., formate, acetate, trifluoroacetate, maleate, tartrate, fumarate, methanesulfonate, benzenesulfonate, toluenesulfonate etc.), salts with a basic or acidic amino acid (e.g., arginine, aspartic acid, glutamic acid etc.) and the like.

In the present invention, in vivo and in vitro mean as they are generally used in this field. Namely, "in vivo" means a state where functions and reactions of the target living organism can be expressed in living organisms, and "in vitro" means that such functions and reactions can be expressed in vitro (tissue culture system, cell culture system, cell-free system etc.).

Soft tissue sarcomas include malignant fibrous histocytoma, liposarcoma, rhabdomyosarcoma, leiomyosarcoma, synovial sarcoma, fibrosarcoma, malignant schwannoma, angiosarcoma, clear cell sarcoma and the like.

In addition, gene diagnosis of SYT-SSX protein expressing synovial sarcoma enables selection of patients before treatment, for whom the histone deacetylase inhibitor of the present invention proves effective.

The therapeutic agent for soft tissue sarcoma of the present invention can be used in the form of a pharmaceutical preparation such as a solid, semisolid or liquid preparation (tablet, pellet, troche, capsule, suppository, cream, ointment, aerosol, powder, liquid, emulsion, suspension, syrup, injection etc.) containing a histone deacetylase inhibitor as an active ingredient, which is suitable for transrectal, intranasal, pulmonary, vaginal, external (topical), oral or parenteral (including subcutaneous, implantation, intravenous and intramuscular) administration.

The therapeutic agent for soft tissue sarcoma of the present invention can be also produced by conventional methods using various organic or inorganic carriers conventionally used for forming pharmaceutical preparations, such as excipients (e.g., sucrose, starch, mannitol, sorbitol, lactose, glucose, cellulose, talc, calcium phosphate, calcium carbonate etc.), condensation agents (e.g., cellulose, methyl cellulose, hydroxypropyl cellulose, polypropylpyrrolidone, gelatin, gum arabic, polyethylene glycol, sucrose, starch etc.), disintegrants (e.g., starch, carboxymethyl cellulose, carboxymethyl cellulose calcium, hydroxypropyl starch, sodium starch glycolate, sodium hydrogen carbonate, calcium phosphate, calcium citrate etc.), lubricants (e.g., magnesium stearate, aerosil, talc, sodium lauryl sulfate etc.), corrigents (e.g., citric acid, menthol, glycine, orange powder etc.), preservatives (e.g., sodium benzoate, sodium hydrogen sulfite, methylparaben, propylparaben etc.), stabilizers (citric acid, sodium citrate, acetic acid etc.), suspensions (e.g., methyl cellulose, polyvinyl pyrrolidone, aluminum stearate etc.), dispersants (e.g., hydroxypropylmethyl cellulose etc.), diluents (e.g., water etc.), wax base materials (e.g., cacao butter, polyethylene glycol, white petrolatum etc.) and the like.

While the administration method of the therapeutic agent for soft tissue sarcoma of the present invention is not particularly limited, intravenous, intramuscular or oral administration is preferable. In addition, while a therapeutically effective amount of HDACi's, such as, compound A or compound B or a pharmaceutically acceptable salt thereof, when it is used for a human as an active ingredient varies depending on the age and condition of individual patient to be treated, and the kind of soft tissue sarcoma, in the case of an intravenous administration, the daily dose of compound A and compound B is generally 0.1–100 mg, preferably 1–50 mg, more preferably 5–30 mg, in the amount of compound A, per 1 $m^2$ of human body surface area, which is given for the treatment of sarcoma by continuous infusion.

Furthermore, the HDACi's in the present invention can be administered alone or in combination with an additional anti-tumor treatment, such as surgery, radiation therapy and/or chemotherapy. Examples of chemotherapeutic agents include DNA cross-linkers, alkylating antitumor agents, antimetabolite antitumors, and taxanes. Preferred chemotherapeutic agents include cipslatin, 5-fluorouracil, paclitaxel (taxol), docetaxel, and the like.

EXAMPLES

The present invention is specifically explained in detail in the following by referring to Examples, which are not to be construed as limitative.

Example 1

An SYT-SSX protein expressing synovial sarcoma cell line HS-SY-2 (established and kindly provided by Dr. Hiroshi Sonobe, Department of Pathology, National Fukuyama Hospital), YaFuSS (established and kindly provided by Dr. Junya Toguchida, Department of Tissue Regeneration, Institute for Frontier Medical Sciences, Kyoto University) and SYO-1 (established and kindly provided by Dr. Akira Kawai, Department of Orthopedics, Faculty of Medicine, Okayama University (now Department of Orthopedics, National Cancer Center)) were cultured in DMEM (Dulbecco's modified Eagle's medium) containing 10%(v/v) fetal bovine serum (FBS), 100 U/ml penicillin and 100 μg/ml streptomycin at 37° C. under 5% $CO_2$ environment. These cells were plated and cultured for 24 hr, detached with 0.25%(w/v) trypsin and recovered. For cell growth ability, an MTT analysis kit (Colorimetric (MTT) assay for cell survival and proliferation kit of CHEMICON International, Inc.) was used. Each cell strain was plated in a 96 well microtiter plate at $10^3$ cell/well, and after culture for 24 hr, exposed to a 0.1%(v/v) dilute ethanol solution of FK228 at a concentration distribution of 0.1 nM, 0.2 nM, 1 nM, 50 nM and 100 nM, and 0.1%(v/v) ethanol (Et-OH 0.1% in FIG. 1) as a control. After exposure for 24 hr, 48 hr and 96 hr, each culture was passed through a 570 nM filter and the absorbance was measured. All were performed with n=4.

Figure 2:
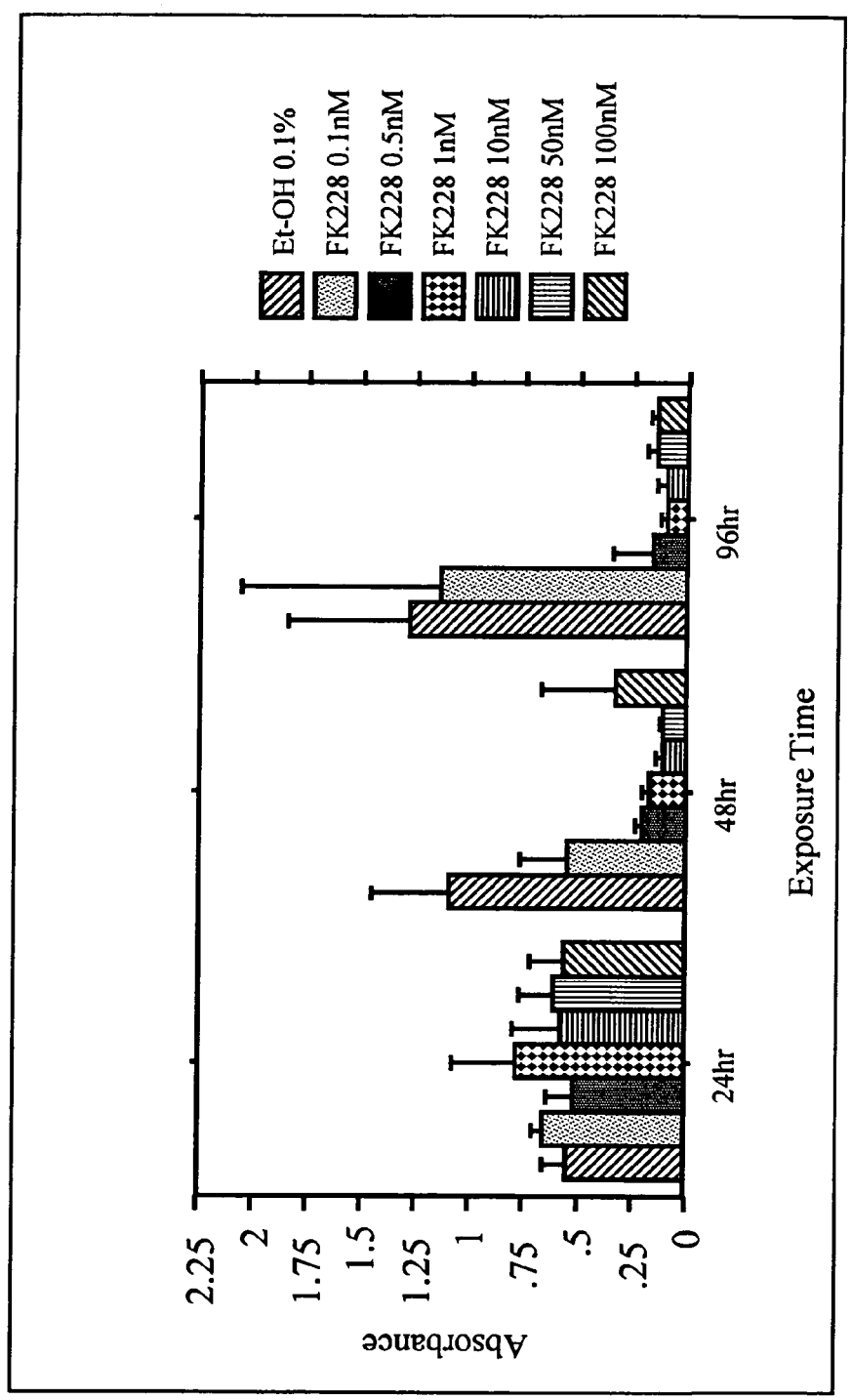
FIG. 2 is a graph showing an in vitro antitumor action of FK228 against YaFuSS synovial sarcoma cell strain, which is one of the SYT-SSX protein expressing synovial sarcoma cell strains.
Figure 3:
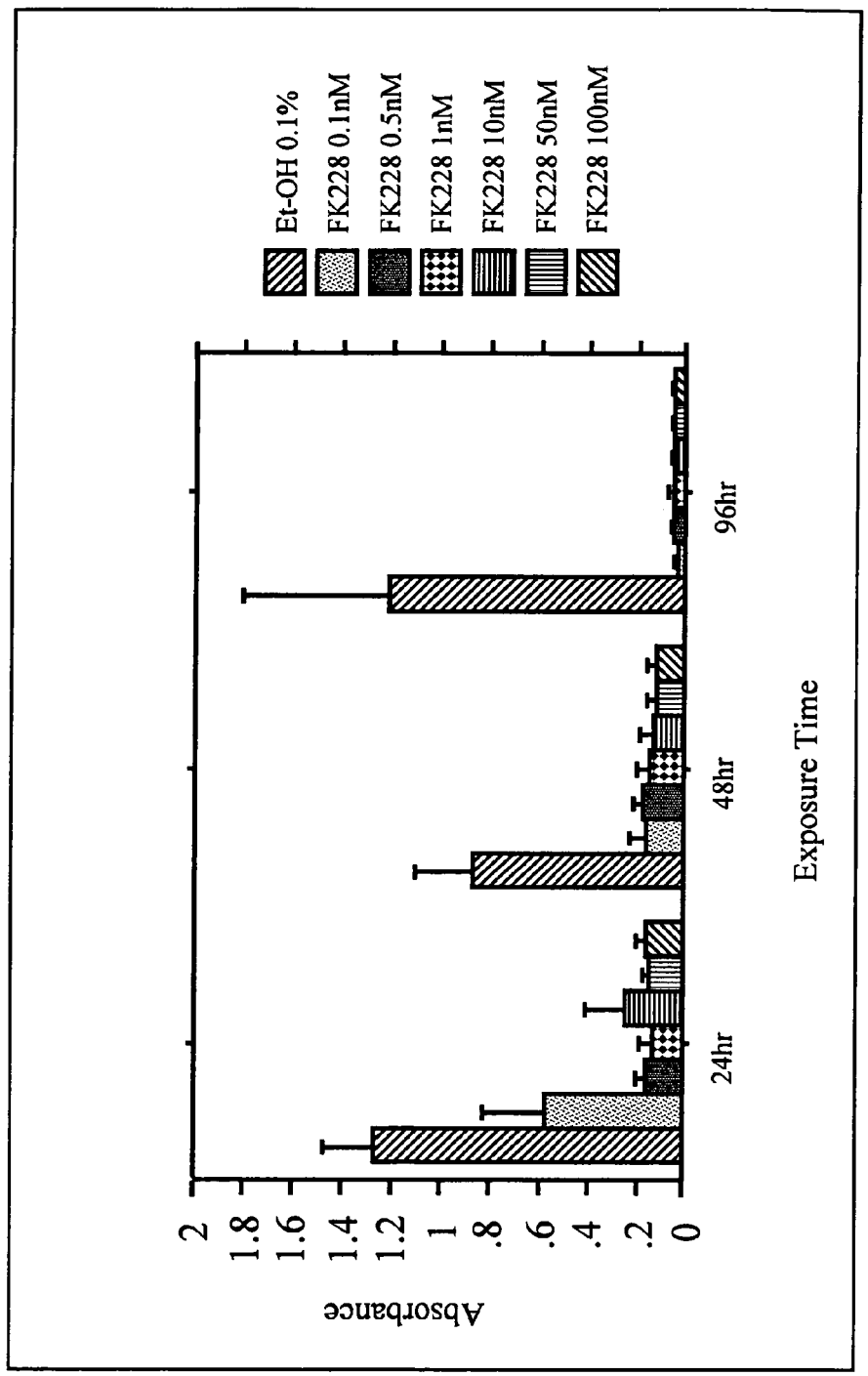
FIG. 3 is a graph showing an in vitro antitumor action of FK228 against SYO-1 synovial sarcoma cell strain, which is one of the SYT-SSX protein expressing synovial sarcoma cell strains.

The results are shown in FIG. 1, FIG. 2 and FIG. 3. FK228 showed an in vitro antitumor effect on SYT-SSX protein expressing synovial sarcoma, a soft tissue sarcoma.

Example 2

Inbred male (BALB/C/nu/nu) nude mice were supplied by Charles River Japan, Inc. The animals were all fed and handled according to the Animal Test Guideline, Animal Resources Division, Advanced Science Research Center, Okayama University. FK228 was administered after 10 days from subcutaneous implantation of $10^5$ cells each of the SYO-1 cell strain. The tumor volume was assumed by measuring two diameters perpendicular to each other using calipers and from the following formula (tumor volume=$\frac{1}{6}\pi$ [(d1×d2)$^{3/2}$] (wherein d1 and d2 are two perpendicular diameters)). The dose was evaluated by intravenously administering a dilute FK228 solution (50 µl, 10% HCO60, which is ployoxyethylene (60) hydrogenated castor oil, diluted with physiological saline) at 0 mg/kg, 1.6 mg/kg or 3.2 mg/kg to 20 animals, and as a control, a 3.2 mg/kg dilute FK228 solution was intravenously injected to 7 animals free of tumor implantation. The administration was performed 3 times every 4 days, the tumor volume was also measured every 4 days, as well as after completion of the administration.

Figure 4:
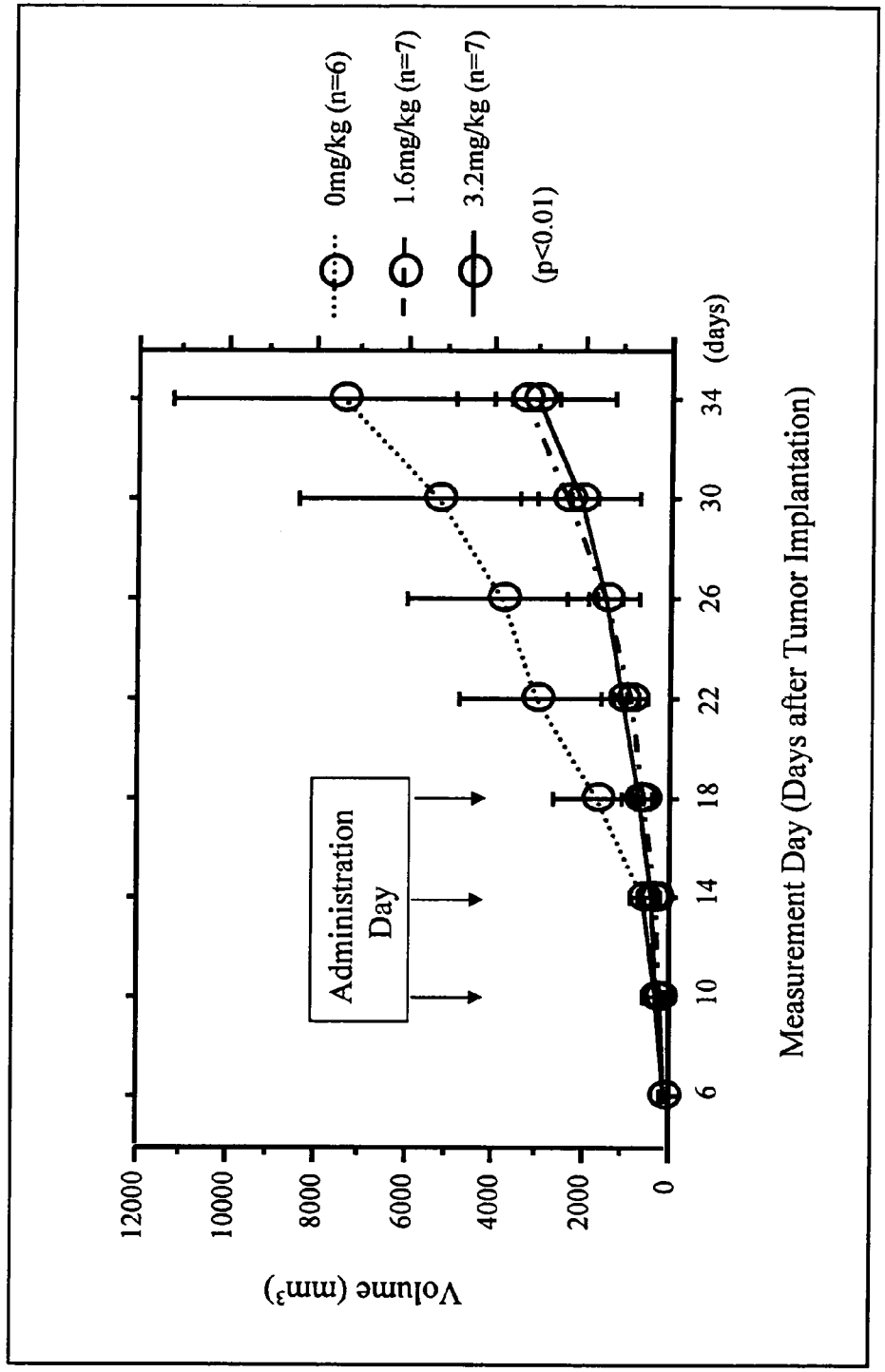
FIG. 4 is a graph showing an in vivo antitumor action of FK228 against SYO-1 synovial sarcoma cell strain, which is one of the SYT-SSX protein expressing synovial sarcoma cell strains.

The results are shown in FIG. 4, wherein the measurement days are shown in terms of the number of days after the subcutaneous implantation. FK228 showed an in vivo antitumor effect on SYT-SSX protein expressing synovial sarcoma, a soft tissue sarcoma.

Example 3

An SYT-SSX protein non-expressing synovial sarcoma cell line HTB93 (which is the ATCC identification number of cell line SW982) (purchased from ATCC: American Type Culture Collection) was cultured in DMEM (Dulbecco's modified Eagle's medium) containing 10%(v/v) fetal bovine serum (FBS), 100 U/ml penicillin and 100 µg/ml streptomycin at 37° C. under 5% $CO_2$ environment. These cells were plated and cultured for 24 hr. detached with 0.25%(w/v) trypsin and recovered. For cell growth ability, an MTT analysis kit (Colorimetric (MTT) assay for cell survival and proliferation kit of CHEMICON International, Inc.) was used. Each cell strain was plated in a 96 well microtiter plate at $2 \times 10^3$ cell/well, and after culture for 24 hr, exposed to a 0.1%(v/v) dilute ethanol solution of FK228 at a concentration distribution of 0.001 nM, 0.01 nM, 0.1 nM, 0.5 nM, 1 nM, 5 nM, 10 nM, 50 nM and 100 nM, 0.1%(v/v) ethanol as a control and the medium alone as a blank. After exposure for 24 hr, 48 hr, 72 hr and 96 hr, each culture was passed through a 570 nM filter and the absorbance was measured. All were performed with n=4.

Figure 5:
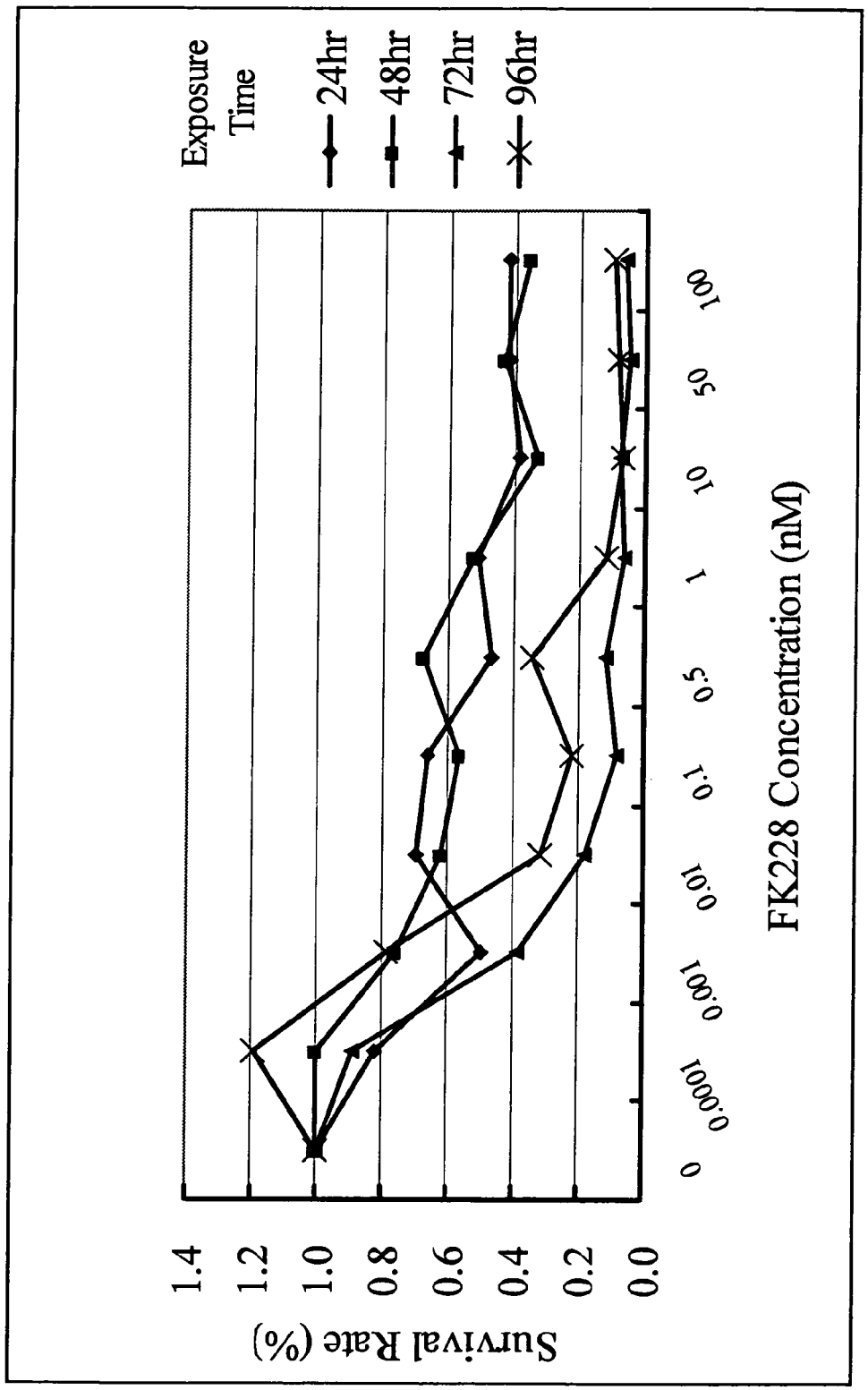
FIG. 5 is a graph showing an in vitro antitumor effect of FK228 on HTB93 synovial sarcoma cell strain, which is one of the synovial sarcoma cell strains that do not express SYT-SSX protein.

For the results, average values of the FK228 addition sample, control and blank were taken, and using numerical values obtained by subtracting a blank value from the value of the FK228 addition sample or control, a percentage corresponding to the ratio of the numerical value of the FK228 addition sample relative to that of the control was taken as survival rate (%). The results are shown in FIG. 5. FK228 showed an in vitro antitumor effect also on SYT-SSX protein non-expressing synovial sarcoma, which is one kind of soft tissue sarcoma.

Sequence Listing Free Text

SEQ ID NO: 1: Xaa is an amino acid represented by the formula $NH_2C(CHCH_3)COOH$.

In the formula $COOHCH_2CH(CHCHC_2H_4SH)OH$, the carboxylic group is bonded with the amino group of the first amino acid Val, the hydroxyl group is bonded with the carboxylic group of the fourth amino acid Val, and the SH group is bonded with the SH group of the second amino acid Cys via a disulfide bond.

INDUSTRIAL APPLICABILITY

The therapeutic agent for soft tissue sarcoma of the present invention, which contains a histone deacetylase inhibitor (particularly FK228) as an active ingredient, has a superior antitumor action not only in vitro but also in vivo. Accordingly, it can be clinically used, particularly preferably for the treatment of soft tissue sarcoma.

While this invention has been shown and described with references to preferred embodiments thereof, it will be understood by those skilled in the art that various changes in form and details may be made therein without departing from the scope of the invention encompassed by the appended claims. All patents and patent publication and other publications identified or referenced herein are incorporated by reference in their entirety.

This application is based on and claims the benefit of patent application No. 183643/2003 filed in Japan, the contents of which are hereby incorporated by reference.

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: SITE
<222> LOCATION: (1), (2), (4)
<223> OTHER INFORMATION: In the formula COOHCH2CH(CHCHC2H4SH)OH, the
      COOH is bonded with the amino group of the first Val, the OH is
      bonded with the carboxylic group of the fourth Val, and the SH
      group is bonded with the SH group of the Cys via a disulfide bond
<220> FEATURE:
<221> NAME/KEY: MISC_FEATURE
<222> LOCATION: (3)..(3)
<223> OTHER INFORMATION: Xaa is an amino acid represented by the formula
      NH2C(CHCH3)COOH
```

```
<400> SEQUENCE: 1

Val Cys Xaa Val
1
```

The invention claimed is:

1. A method for treating soft tissue sarcoma, comprising:
   administering an effective amount of a histone deacetylase inhibitor selected from the group consisting of a compound of formula (I)

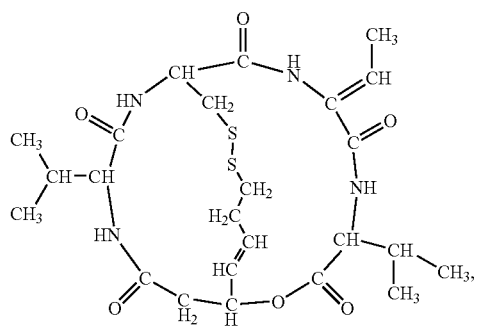

(I)

a thiol form of the compound of formula (I) having a reduced S—S bond, an analog of the compound of formula (I), a prodrug of the compound of formula (I), a pharmaceutically acceptable salt of the compound of formula (I), a hydrate of the compound of formula (I), an anhydrous form of the compound of formula (I), an acetylated form of the compound of formula (I), a stereoisomer of the compound of formula (I), trichostatin A, sodium butyrate, suberoylanilide hydroxamic acid, MS-275, cyclic hydroxamic acid containing peptide, Apicidin, Trapoxin and mixtures thereof;

wherein the soft tissue sarcoma is synovial sarcoma.

2. The method of claim 1, wherein the soft tissue sarcoma is synovial sarcoma.

3. The method of claim 2, wherein the synovial sarcoma is SYT-SSX protein expressing sarcoma.

4. The method of claim 1, wherein the histone deacetylase inhibitor is a compound represented by the formula (II)

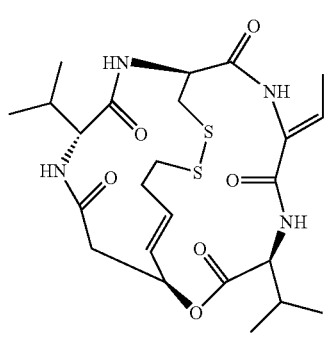

(II)

or a pharmaceutically acceptable salt thereof.

5. The method of claim 4, wherein the soft tissue sarcoma is synovial sarcoma.

6. The method of claim 5, wherein the synovial sarcoma is SYT-SSX protein expressing sarcoma.

* * * * *

UNITED STATES PATENT AND TRADEMARK OFFICE
CERTIFICATE OF CORRECTION

PATENT NO. : 7,056,883 B2
APPLICATION NO. : 10/875382
DATED : June 6, 2006
INVENTOR(S) : Tatsuo Ito et al.

It is certified that error appears in the above-identified patent and that said Letters Patent is hereby corrected as shown below:

Column 10, Claim 1, line 10, should read:

-- wherein the soft tissue sarcoma is selected from the group consisting of malignant fibrous histocytoma, liposarcoma, rhabdomyosarcoma, leiomyosarcoma, synovial sarcoma, fibrosarcoma, malignant schwannoma, angiosarcoma, and clear cell sarcoma. --

Signed and Sealed this

Twenty-third Day of November, 2010

David J. Kappos
*Director of the United States Patent and Trademark Office*